(12) United States Patent
Selsted et al.

(10) Patent No.: US 12,012,440 B2
(45) Date of Patent: Jun. 18, 2024

(54) COMPOSITIONS AND METHODS FOR TREATMENT OF FUNGAL INFECTIONS

(71) Applicant: THE UNIVERSITY OF SOUTHERN CALIFORNIA, Los Angeles, CA (US)

(72) Inventors: Michael E. Selsted, Pasadena, CA (US); Dat Q. Tran, Alhambra, CA (US); Justin B. Schaal, Orange, CA (US); Virginia Basso, West Covina, CA (US)

(73) Assignee: The University of Southern California, Davis, CA (US)

( * ) Notice: Subject to any disclaimer, the term of this patent is extended or adjusted under 35 U.S.C. 154(b) by 0 days.

(21) Appl. No.: 17/358,828

(22) Filed: Jun. 25, 2021

(65) Prior Publication Data

US 2021/0403523 A1    Dec. 30, 2021

Related U.S. Application Data

(60) Provisional application No. 63/044,943, filed on Jun. 26, 2020.

(51) Int. Cl.
*C07K 14/47* (2006.01)
*A61K 38/00* (2006.01)
*A61P 31/10* (2006.01)
*C07K 7/64* (2006.01)

(52) U.S. Cl.
CPC ................ *C07K 14/4723* (2013.01)

(58) Field of Classification Search
CPC ...... C07K 14/4723; C07K 14/47; C07K 7/64; A61K 38/00; A61P 31/10
See application file for complete search history.

(56) References Cited

U.S. PATENT DOCUMENTS

| | | | | |
|---|---|---|---|---|
| 7,119,070 B2* | 10/2006 | Selsted | .................. | A23L 3/3526 514/21.4 |
| 7,462,598 B2* | 12/2008 | Selsted | .................... | A61L 12/14 530/300 |
| 2003/0162718 A1 | 8/2003 | Selsted | | |
| 2013/0157964 A1* | 6/2013 | Selsted | .............. | C07K 14/4723 514/21.1 |
| 2020/0333024 A1* | 10/2020 | Selsted | .................... | A61P 1/04 |

FOREIGN PATENT DOCUMENTS

EP     2990415     11/2018

OTHER PUBLICATIONS

Conibear, et al. The Cyclic Cystine Ladder in Theta Defensins is Important for Structure and Stability, but Not Antibacterial Activity. Division of Chemistry and Structural Biology, University of Queensland, Australia. Feb. 2013. 11 pages.

Doss, Mona, et al. "Hapivirins and Diprovirins: Novel Theta Defensin Analogs with potent Activity Against Influenza A Virus," The Journal of Immunology. Sep. 2020. 12 pages.

* cited by examiner

*Primary Examiner* — Julie Ha
(74) *Attorney, Agent, or Firm* — Fish IP Law, LLP

(57) ABSTRACT

Peptide analogs of a θ-defensin have been developed that provide a biphasic effect in treating disseminated fungal disease and/or associated septic shock. These analogs are active at concentrations below those needed to provide a fungicidal effect, and function by initially mobilizing effector cells of the immune system to address the infective organism followed by regulation of the immune system to down regulate the inflammatory response. These θ-defensin analogs are protective at concentrations where naturally occurring θ-defensins have no apparent effect, and include a core set of structural and sequence features not found in native θ-defensins.

11 Claims, 17 Drawing Sheets

Specification includes a Sequence Listing.

Cyclic Peptide 1
(SEQ ID NO. 2)

Cyclic Peptide 2
(SEQ ID NO. 3)

Cyclic Peptide 3
(SEQ ID NO. 4)

Cyclic Peptide 4
(SEQ ID NO. 5)

Cyclic Peptide 5
(SEQ ID NO. 6)

Cyclic Peptide 6
(SEQ ID NO. 7)

COMPOSITIONS AND METHODS FOR TREATMENT OF FUNGAL INFECTIONS

This application claims the benefit of U.S. Provisional Patent Application No. 63/044,943 filed on Jun. 26, 2020. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

This invention was made with government support under Grant Nos. AI142959 and AI125141, awarded by the National Institutes of Health (NIH). The government has certain rights in the invention.

FIELD OF THE INVENTION

The field of the invention is biomedicine, specifically peptide drugs.

BACKGROUND

The background description includes information that may be useful in understanding the present invention. It is not an admission that any of the information provided herein is prior art or relevant to the presently claimed invention, or that any publication specifically or implicitly referenced is prior art.

Superficial fungal infections, such as those of the mucous membranes of the mouth and genitals, are relatively common and are rarely life threatening. Systemic or disseminated fungal infections, however, can have a mortality rate ranging from 30% to 50%. Fungal pathogens are a major cause of hospital-acquired infection, particularly among surgical patients and those with indwelling catheters. Increased risk of systemic fungal infection is also associated with decreased immune function, neutropenia, and diabetes. An increased risk of systemic or dissemination fungal infection is also associated with the use of biologic therapies for treatment of inflammatory or autoimmune diseases, which selectively suppress components of the immune response.

Systemic fungal infections are typically caused by *Candida* spp. (such as *C. albicans*), which are essentially ubiquitous and hence not easily avoided. While antifungal drugs are available resistant or multiple drug resistant strains are becoming increasingly prevalent. Unfortunately, systemic infections caused by multiple drug resistant fungi are a growing global health concern. Approximately 1.5 million cases of disseminated mycoses occur annually and are associated with high mortality rates.

The growing incidence of multiple drug resistant *Candida* spp. infections has contributed to the increase in mortality from systemic candidiasis. A major risk factor for systemic candidiasis is the presence of biofilms, which frequently develop on implanted medical devices such as venous catheters. Such biofilms are notoriously resistant to antifungal therapy and are a common source of blood borne dissemination of fungal pathogens.

Development of effective and relatively nontoxic antifungal drugs has proven challenging. There are currently only three classes of antifungal drugs used for treatment of invasive fungal infections: polyenes, azoles, and echinocandins. Of these echinocandins are the most recently approved class of antifungals, and were first introduced nearly 30 years ago. Limitations associated with use of currently available antifungal drugs include limited range of molecular targets, serious adverse side effects, and lack of activity against biofilms. The emergence of multiple drug resistant fungal pathogens underscores the urgent need for development of novel approaches to the treatment of fungal infections.

Defensins are a diverse family of small antimicrobial proteins that are part of the body's nonspecific defense against infection. There are three different and structurally distinct classes of defensin proteins: alpha, beta, and theta defensins. The α and β defensins are linear, tri-disulfide containing peptides having molecular weights of about 2.6 kDa or 4.5 kDa, respectively. In contrast, θ-defensins are cyclic peptides (i.e. circular peptides wherein the backbone is formed by sequential peptide bonds with neither a free amino or carboxyl terminus) composed of 18 amino acids.

θ-defensins are expressed in tissues of rhesus monkeys, baboons, and other Old World monkeys. They are not present in humans and other hominids. Naturally occurring θ-defensins are composed of 18 backbone cyclized (i.e. through the alpha-amine groups rather than side chain moieties) peptides stabilized by three disulfide bonds. These three disulfide bonds are conserved among all known θ-defensins. θ-defensins were originally discovered and classified as defensins based on the antimicrobial properties of the peptides. More recently it has been found that θ-defensins can have potent immunomodulatory effects.

International Patent Application Publication No. WO 2007/044998 (to Lehrer et al) describes relationships between structure and biological activity for retrocyclin peptides and analogs of such peptides that include varying degrees of enantiomer content in an attempt to derive structure/activity relationships. These analogs, however, retain the length and structure of the native retrocyclin. In addition, the reference is only instructive for antibacterial activity.

Peptide analogs of various defensins have been investigated. For example, European Patent Application EP2990415 (to Colavita et al) describes circularized analogs of a β-defensin that show improved antibiotic effectiveness relative to the parent protein. Such β-defensins, however, have been shown to stimulate release of pro-inflammatory cytokines, which raises safety concerns and limits their utility.

United States Patent Application Publication No. US 2003/0022829 (to Maury et al) describes synthesis and biologic activity of chimeric θ-defensins and speculates on the possibility of making conservative amino acid substitutions, however these appear to retain the length and structure of native θ-defensins. U.S. Pat. No. 10,512,669 (to Selsted et al) describes several tetradecapeptide θ-defensin analogs derived from RTD-1, and their biological properties.

There remains, therefore, a need for safe and effective compounds for the management and/or treatment of fungal infections, particularly disseminated fungal infections.

SUMMARY OF THE INVENTION

The inventive subject matter provides synthetic analogs of θ-defensins that have improved activity in treating fungal infections (in particular, disseminated or systemic fungal infections) relative to native θ-defensins. These peptides act through host directed mechanisms and are effective at concentrations that are below those at which the analogs have direct fungicidal and/or fungistatic effect(s) against the same pathogen in vitro.

One embodiment of the inventive concept is a cyclic peptide consisting of 14 amino acids and having a structure as shown in FIG. 7A, which includes two disulfide bonds between two pairs of cysteines, where AA3 and AA12 are cysteines joined by a disulfide bond, AA5 and AA10 are cysteines joined by a disulfide bond, AA4 is serine or a first hydrophobic amino acid, AA11 is serine or a second hydrophobic acid, AA6 is arginine, AA7 is arginine, AA8 is arginine, and wherein the cyclic peptide comprises five arginine residues that provide a positively charged content of at least about 36% at physiological pH. In some embodiments the first hydrophobic amino acid and the second hydrophobic amino acid are leucine or isoleucine. In some embodiments AA1 is glycine. In some embodiments AA2 is a third hydrophobic amino acid, such as valine or leucine. In some embodiments AA9 is a fourth hydrophobic amino acid, such as valine or phenylalanine. In some embodiments AA13 and AA14 are arginine. In some embodiments AA4 cannot be alanine or serine. In some embodiments AA11 cannot be alanine.

Another embodiment is a cyclic peptide consisting of 14 amino acids and having a structure as shown in FIG. 7A, which includes two disulfide bonds between two pairs of cysteines, where AA3 and AA12 are cysteines joined by a disulfide bond, AA5 and AA10 are cysteines joined by a disulfide bond, AA4 is arginine, AA11 is arginine, two of AA6, AA7, and AA8 are arginine, and wherein the cyclic peptide comprises five or more arginine residues that provide a positively charged content of at least about 36% at physiological pH.

Such a cyclic peptide can be an analog of a θ-defensin that provides improved survival when applied systemically in a murine model of disseminated fungal infection relative to the θ-defensin itself. In some embodiments the cyclic peptide provides a biphasic response on application to a murine model of sepsis. Such a biphasic response includes a first phase of mobilization of host effector cells having antifungal activity and a second phase of moderation of host inflammatory response. In some embodiments the cyclic peptide has a TACE inhibiting activity, and/or suppresses at least one of expression, processing, and release of TNF.

Such cyclic peptides retain activity following exposure to environmental extremes of temperature, low pH, freezing and/or thawing, and dissolution in a biological matrix (such as blood, plasma, or serum. In some embodiments such cyclic peptides are non-immunogenic at doses effective to treat or prevent disseminated fungal disease and associated septic shock. Such cyclic peptides can activate a host immune system to enhance host clearance of pathogens, and can also have an activity that modulates inflammation to enhance disease resolution and survival at doses effective to treat or prevent septic shock.

Another embodiment of the inventive concept is a method of treating or preventing septic shock and/or severe sepsis by administering a cyclic peptide as described above to an animal at risk of disseminated fungal disease.

Another embodiment of the inventive concept is the use of a cyclic peptide as described above in treating or preventing disseminated fungal disease and/or associated septic shock and/or severe sepsis, or the use of such a cyclic peptide in preparing a medicament that is effective in treating or preventing disseminated fungal disease and/or septic shock.

Various objects, features, aspects and advantages of the inventive subject matter will become more apparent from the following detailed description of preferred embodiments, along with the accompanying drawing figures in which like numerals represent like components.

RTD-1 were applied, and fungal growth monitored. MFC was determined as the lowest concentration that provided 99% killing relative to the input inoculum. MIC was determined as the lowest concentration that inhibited growth. Results are shown in Table 1.

TABLE 1

| | RPMI | | | | | | 50% serum | |
|---|---|---|---|---|---|---|---|---|
| | RTD-1 | | Fluconazole | | Caspofungin | | RTD-1 | |
| C. albicans strain # | MIC µg/mL | MFC µg/mL | MIC µg/mL | MFC µg/mL | MIC µg/mL | MFC µg/mL | MIC µg/mL | MFC µg/mL |
| SC5314 | 12.5 | 25 | 64 | >256 | 0.06 | >256 | >100 | >100 |
| 43001 | 6.25 | 12.5 | >256 | >256 | 2 | 2 | >100 | >100 |
| 53264 | 12.5 | 12.5 | >256 | >256 | >8 | >8 | >100 | >100 |

Figure 16:
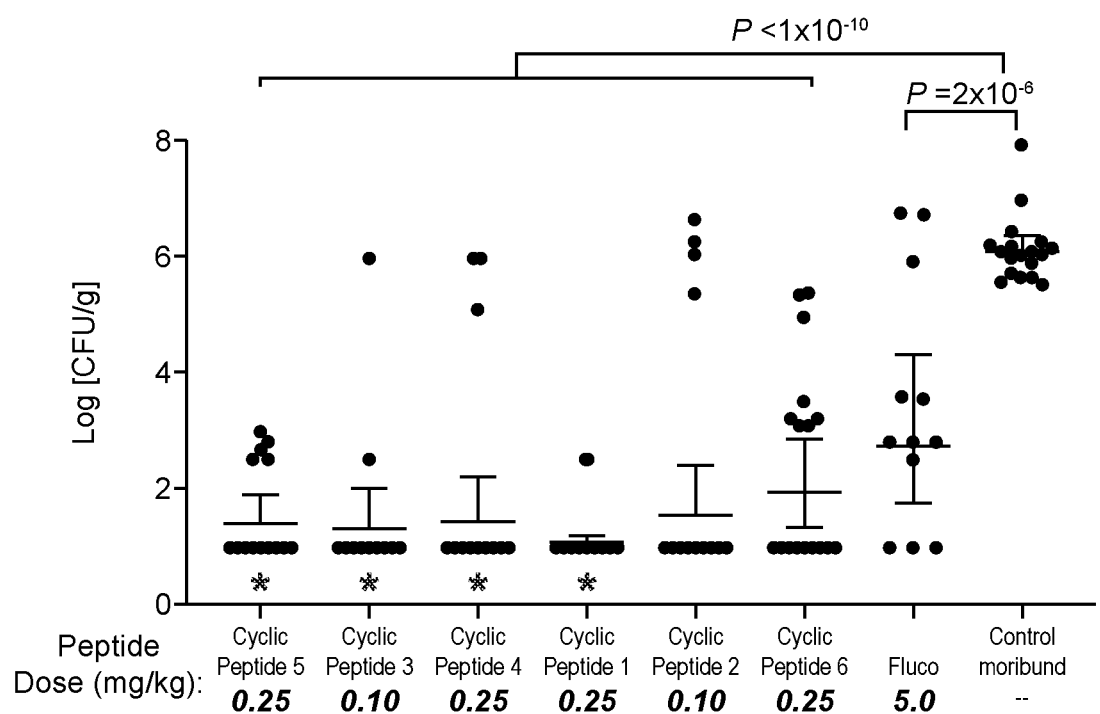

FIG. 16 shows the results of studies of fungal clearance in a murine model of disseminated candidiasis on treatment with fluconazole (Fluco), and synthetic cyclic tetradecapeptides of the inventive concept.

DETAILED DESCRIPTION

The inventive subject matter provides novel peptides that induce a biphasic effect in treating fungal infection (such a disseminated fungal infection) using host mediated processes. Such peptides can act by initially recruiting effector cells of the immune system to address the infective fungal organism followed by regulation of the immune system to regulate the inflammatory response. The novel peptides are analogs of naturally occurring θ-defensins with sequences that have been modified to provide an indirect antifungal effect via recruitment of effector cells of the host immune system and to prevent and/or treat sepsis/septic shock. These novel θ-defensin analogs are effective at sub-antifungal plasma concentrations that do not provide a direct antifungal effect (i.e. that do not generate a fungicidal or a fungistatic effect when applied at such a concentration in vitro) in the absence of host innate immune effectors. Such θ-defensin analogs can be protective at concentrations where native θ-defensins have no apparent effect, and include a core set of structural and sequence features not found in native θ-defensins.

Within the context of this application, a "sub-antifungal concentration" in regard to a fungal pathogen should be understood to be a concentration at which the compound so described has no antifungal effect when applied to the fungal pathogen in vitro (e.g. in a liquid culture medium), e.g. in the absence of host immune effectors For example, a sub-antifungal concentration of a compound in regard to C. albicans would be a concentration that is less than that which demonstrates an antifungal effect against the organism in an in vitro setting (e.g. in the absence of host immune effectors).

Basso et al. (Basso et al., "Rhesus theta defensin 1 promotes long term survival in systemic candidiasis by host directed mechanisms" Nature Scientific Reports (2019) 9:16905) provides an example of determination of sub-antifungal concentration for the native θ-defensin RTD-1 in regard to different strains of Candida albicans. Cultures of different strains of C. albicans were established in RPMI media or RPMI media containing 50% serum. Different amounts of fluconazole (Fluco), caspofungin (Caspo), or Based on such data, for C. albicans a sub-antifungal concentration of RTD-1 in the presence of serum would be less than 100 µg/mL. Such sub-antifungal concentrations can be determined experimentally (for example, by culture from a patient sample) or, preferably, from historical data.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

One should appreciate that the disclosed peptides provide many advantageous technical effects, including provision of a biphasic response that is effective in reducing mortality from disseminated or systemic fungal infection and associated sepsis or shock when administered in low, sub-antifungal amounts.

Recently, Basso et al. (Basso et al., "Rhesus theta defensin 1 promotes long term survival in systemic candidiasis by host directed mechanisms" Nature Scientific Reports (2019) 9:16905) have shown that the naturally occurring θ-defensin RTD-1 (SEQ ID NO. 1) is effective in animal models of systemic candidiasis for both susceptible and multiple drug resistant strains of *C. albicans*. This paper is incorporated herein by reference. While RTD-1 was effective in in vitro studies, the antifungal activity was abolished by the presence of serum and required 50-fold or higher concentrations than were found to be effective in vivo in murine animal model studies. Such in vivo studies showed both antifungal activity and a reduction in long term production of pro-inflammatory cytokines on treatment with RTD-1, both of which contribute to recovery from disseminated fungal infection and a reduction in potentially harmful sequelae from such infection. As shown below, novel synthetic analogs of θ-defensins can provide similar or improved activity.

Figure 1:
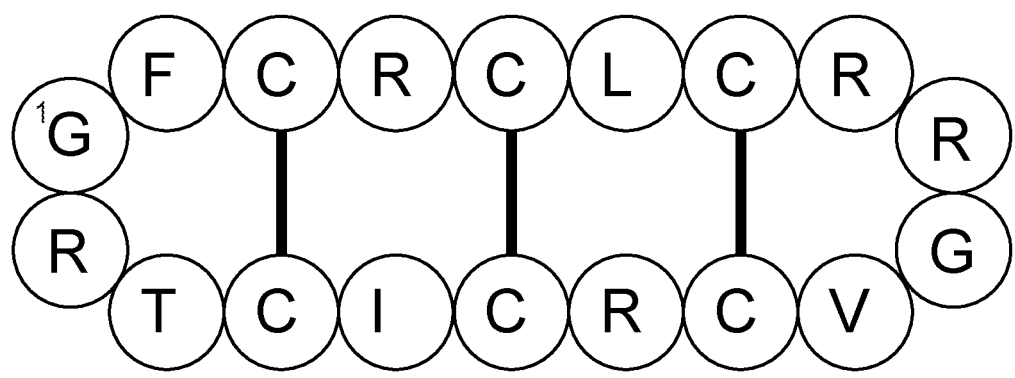
FIG. 1 shows a schematic depiction of the naturally occurring θ-defensin RTD-1 (SEQ ID NO. 1).

Inventors have developed synthetic cyclic tetradecapeptide analogs of the θ-defensin RTD-1 that demonstrated at least some of the antifungal activities of the parent peptide, despite their smaller size and reduced number of disulfide bonds. The structure of RTD-1 is shown in FIG. 1. As shown, RTD-1 (which is expressed naturally in rhesus monkeys) is a cyclic octadecapeptide that includes 3 pairs of cysteines coupled by disulfide bonds that transit the circular primary structure of the peptide.

Figure 2:
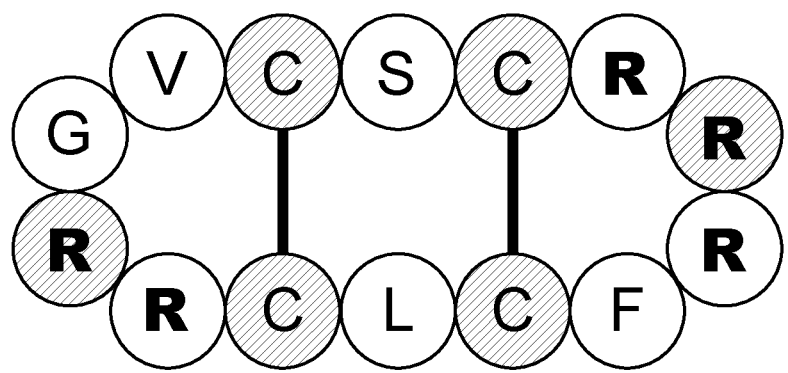
FIG. 2 shows a schematic depiction of the synthetic θ-defensin analog Cyclic Peptide 1 (SEQ ID NO. 2).
Figure 3:
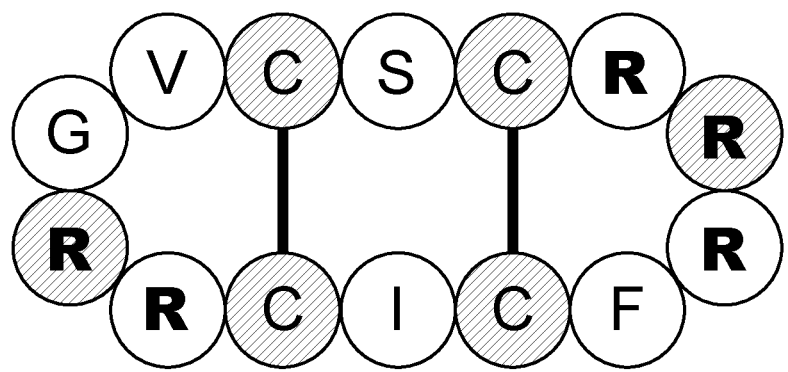
FIG. 3 shows a schematic depiction of the synthetic θ-defensin analog Cyclic Peptide 2 (SEQ ID NO. 3).
Figure 4:
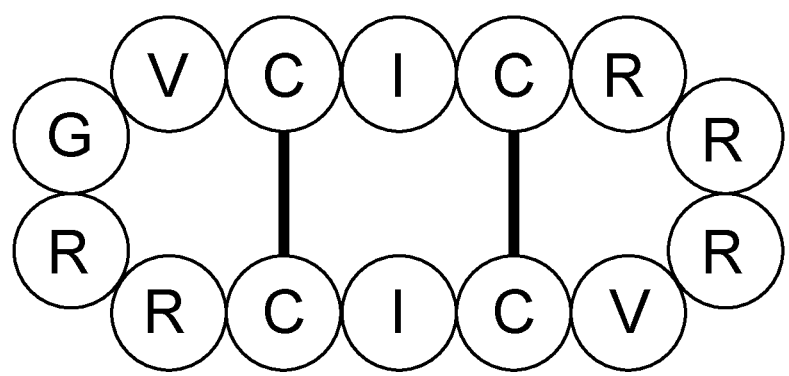
FIG. 4 shows a schematic depiction of the synthetic θ-defensin analog Cyclic Peptide 3 (SEQ ID NO. 4).
Figure 5:
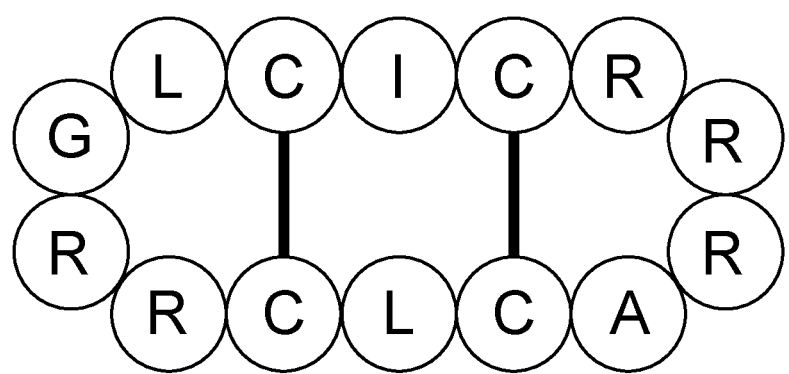
FIG. 5 shows a schematic depiction of the synthetic θ-defensin analog Cyclic Peptide 4 (SEQ ID NO. 5).
Figure 6:
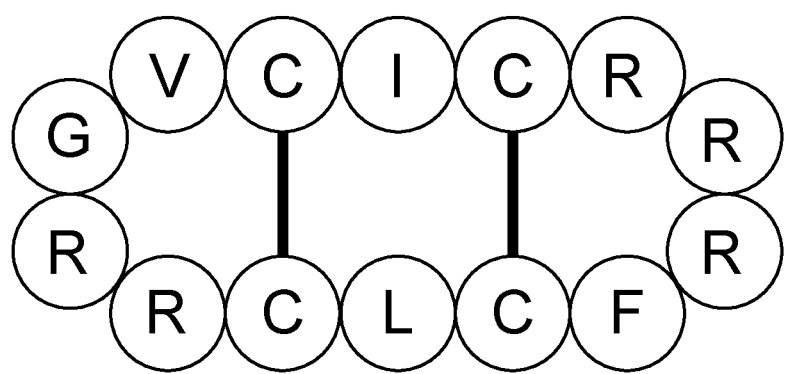
FIG. 6 shows a schematic depiction of the synthetic θ-defensin analog Cyclic Peptide 5 (SEQ ID NO. 6).
Figure 8:
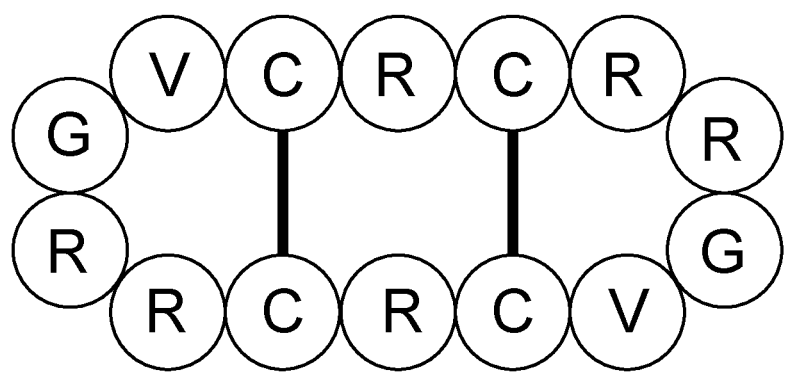
FIG. 8 shows a schematic depiction of the synthetic θ-defensin analog Cyclic Peptide 6 (SEQ ID NO. 7).

A number of examples of synthetic (i.e. non-naturally occurring) analogs of RTD-1 are shown in FIGS. 2 to 6 and FIG. 8. FIG. 2 shows the cyclic structure of the θ-defensin analog Cyclic Peptide 1 (SEQ ID NO. 2). FIG. 3 shows the cyclic structure of the θ-defensin analog Cyclic Peptide 2 (SEQ ID NO. 3). FIG. 4 shows the cyclic structure of the θ-defensin analog Cyclic Peptide 3 (SEQ ID NO. 4). FIG. 5 shows the cyclic structure of the θ-defensin analog Cyclic Peptide 4 (SEQ ID NO. 5). FIG. 6 shows the cyclic structure of the θ-defensin analog Cyclic Peptide 5 (SEQ ID NO. 6), used as a model compound in these studies. FIG. 8 shows the cyclic structure of the θ-defensin analog Cyclic Peptide 6 (SEQ ID NO. 7). Each of the exemplary synthetic analogs is a tetradecapeptide that includes 2 pairs of cysteines coupled by disulfide bonds. These disulfide bonds transit the circular primary structure of the synthetic peptides to form a "box" substructure that incorporates additional amino acids. It should be appreciated that these exemplary analogs show varying degrees of sequence identity with RTD-1, and in some instances show conservative amino acid substitutions near and between the "box" defined by cysteines of the synthetic peptide analogs.

Inventors have prepared and screened a series of θ-defensin analogs that have substantial in vivo antifungal activity and provide long term survival of mice in a model of disseminated candidiasis. These effects at surprisingly low concentrations that are well below those at which direct antifungal activity is found for the model pathogen in vitro. Without wishing to be bound by theory, Inventors believe that the observed antifungal effects are due to modulation of host immune effectors. It should be appreciated that long term survival of disseminated fungal infection requires both management of the infecting organism and of the shock induced by the host response to the infection, either of which can lead to death.

While examples of activity against disseminated fungal infection are provided, Inventors believe that θ-defensin analogs as described herein can be effective at treating other fungal infections, such as topical fungal infections (e.g. thrush). In addition, Inventors believe that θ-defensin analogs as described herein can be utilized in the treatment of a variety of conditions resulting from dysregulation of the immune or inflammatory response, including chronic conditions. Examples of such chronic conditions include rheumatoid arthritis and inflammatory bowel disease.

The Inventors note that θ-defensins have been found to have antiviral activity, and believe that θ-defensin analogs of the inventive concept can similarly provide anti-viral activity, and can prove useful in treating viral disease and inflammatory sequelae of viral infection. Such treatment includes prophylaxis and/or active disease. In some embodiments active disease so treated is symptomatic. In other embodiments active disease so treated is asymptomatic.

Surprisingly, θ-defensin analogs were identified that provide a biphasic response in modulating the immune system in response to systemic fungal infection. The initial effect is mobilization of neutrophils, resulting in clearance of the fungal pathogen. This serves to combat infection, and surprisingly was found to occur at concentrations of the θ-defensin analog that failed to demonstrate an antifungal effect against the model pathogen in vitro. Following this initial mobilization effect these synthetic θ-defensin analogs exhibit a longer term immunomodulatory effect (for example, reducing TNF, IL-6 and other inflammatory cytokines) that contributes to long term survival and in preventing septic shock resulting from disseminated fungal infection.

Figure 7A:
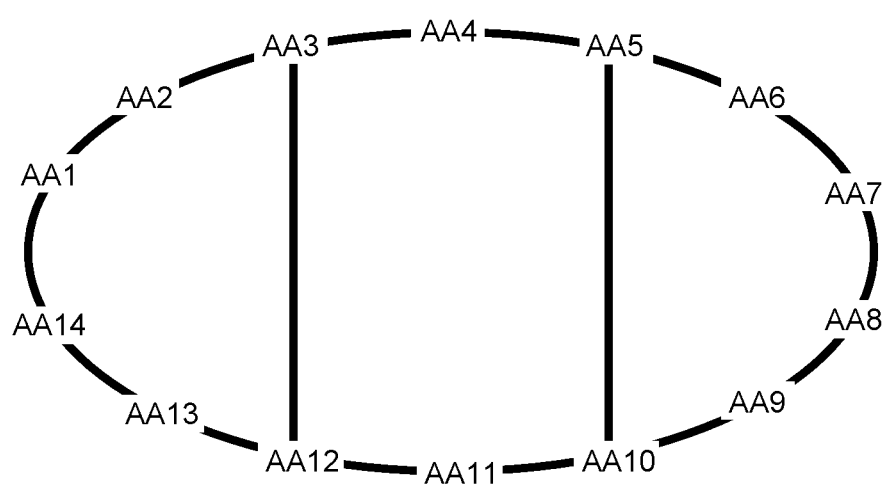
FIG. 7A depicts a numbering system utilized for designation of specific amino acids within the cyclic tetradecapeptides described herein, in the absence of discrete amine- and carboxy-termini found in conventional linear peptides.
Figure 7B:
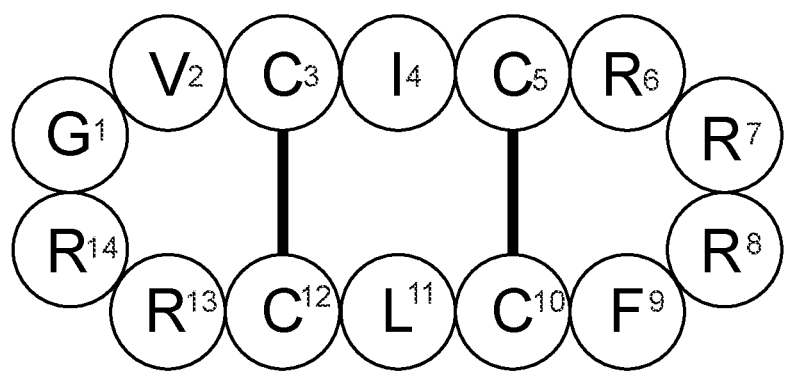
FIG. 7B depicts this numbering system as applied to Cyclic Peptide 5 (SEQ ID NO. 6).

As noted above, examples of a naturally occurring θ-defensin and exemplary θ-defensin analogs are shown in FIGS. 1 to 6 and FIG. 8. It should be appreciated that these cyclic peptides are cyclized through the peptide backbone, and therefore lack conventional amino- and carboxyl-termini. As such amino acid sequence information as provided in accompanying amino acid sequence listings should not be construed as descriptive of a discrete N-terminus or C-terminus for these θ-defensin analogs. Within the context of this application, amino acid position is identified using numerical designations based upon common structural features of the θ-defensin analogs as shown in FIG. 7A. As shown, each position along the cyclic tetradecapeptide chain has a numerical designation. Application of this numbering scheme to the model synthetic cyclic tetradecapeptide Cyclic Peptide 5 (shown in FIG. 6) is depicted in FIG. 7B. For such 14-amino acid analogs, it should be appreciated their three dimensional structures include a first β-turn formed by amino acids 6 to 9 and a second β-turn formed by amino acids 13, 14, 1, and 2 as designated using a numbering system adapted for use with cyclic θ-defensins and their analogs and as shown in FIGS. 7A and 7B.

Suitable cyclic tetradecapeptides can be identified by screening against a murine model for disseminated candidiasis. *C. albicans* SC5314 obtained from American Type Culture Collection can be used as a suitable reference strain. In preferred embodiments one or more strains of resistant *C. albicans* and/or *C. albicans* demonstrating resistance to two or more antifungal drugs can be used. Typical antifungal drugs include caspofungin and fluconazole. Cyclic tetradecapeptides to be tested and antifungal drugs can be suspended or dissolved in water or isotonic saline and administered by subcutaneous, intramuscular, intravenous and/or intraperitoneal injection.

In vitro activity of synthetic cyclic tetradecapeptides and antifungal compounds can be determined using conventional culture techniques that are known in the art as described above in relation to RTD-1, and can be used to determine sub-antifungal concentrations. Systemic or disseminated candidiasis can be modeled in vivo by, for example, challenging inbred BALB/c or outbred CD-1 female mice with 0.15 to 2 mL of *C. albicans* (reference strain or resistant strain) at from about $2\times10^5$ to about $2\times10^7$ CFU/mL of the organism. Animals can the be treated with candidate synthetic cyclic tetradecapeptide before challenge with the pathogen, at the time of pathogen challenge, or after challenge with the pathogen. Antifungal drugs and/or candidate synthetic cyclic tetradecapeptide can be administered subcutaneously, intramuscularly, intravenously and/or intraperitoneally in such an in vivo model of systemic or disseminated candidiasis.

Inventors have identified a number of novel θ-defensin analogs that show significant antifungal activity in vivo. Amino acid sequences of exemplary cyclic peptides are shown in Table 2. It should be appreciated that amino acids identities are indicated using the numerical designation for corresponding positions within the cyclic structures as established in FIG. 7A.

Peptides Cyclic Peptide 1, Cyclic Peptide 2, Cyclic Peptide 3, and Cyclic Peptide 4 show common structural features with Cyclic Peptide 5, which the Inventors believe would be found in common with other synthetic cyclic tetradecapeptides that show antifungal and anti-inflammatory activity in in vivo models of disseminated fungal disease.

Cyclic Peptide 6 differs significantly from the model peptide Cyclic Peptide 5 in interposing arginine between cysteines involved in the disulfide bonds of the peptide (i.e. within the "C-X-C box") and in not including a triplet of consecutive (i.e., adjacent) arginines within the first β turn as defined by amino acids 6, 7, 8, and 9 in Table 2. Inventors believe that Cyclic Peptide 6 represents a different family of synthetic cyclic tetradecapeptide θ-defensin analogs than that represented by Cyclic Peptide 1, Cyclic Peptide 2, Cyclic Peptide 3, and Cyclic Peptide 4. Inventors further believe that synthetic cyclic tetradecapeptides including a plurality of arginines within the C-X-C box structure delimited by a two pairs of disulfide-linked cysteines and/or lacking the characteristic triplet of consecutive/adjacent arginines at positions 6, 7, and 8 can have significant antifungal activity in in vivo models of disseminated fungal infection.

Figure 9:
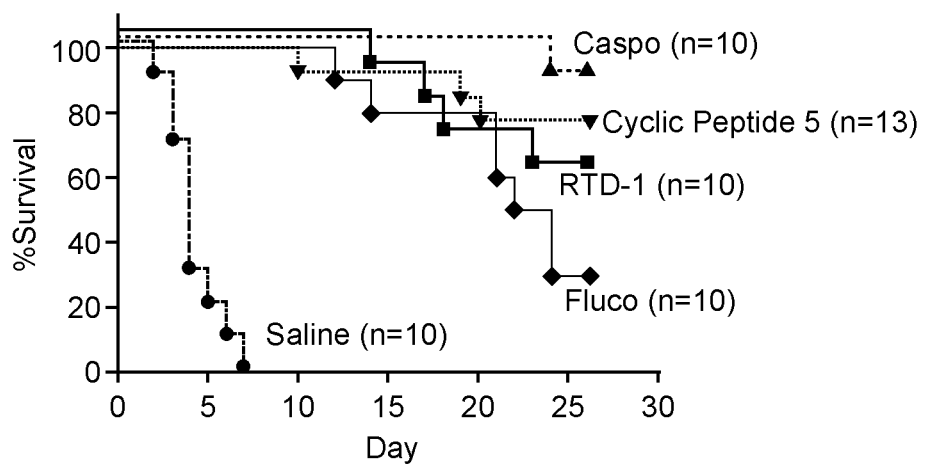
FIG. 9 shows typical results from a study of the effects of RTD-1, the synthetic cyclic tetradecapeptide Cyclic Peptide 5 and two antifungal drugs in an in vivo model of disseminated candidiasis. Mice were infected i.v. at T=0 with $3 \times 10^5$ blastospores of *C. albicans* genetically defined reference strain SC5314. At T=24 h, mice were treated i.p. daily for 7 d with saline, 5 mg/kg caspofungin (Caspo), 5 mg/kg fluconazole (Fluco), 5 mg/kg RTD-1, or 0.25 mg/kg Cyclic Peptide 5. Mice were observed for 26 days p.i, and survival of treated mice was compared to saline controls by log-rank analysis: for RTD-1, Caspo, and Fluco, $P=3.4 \times 10^{-6}$; 0.25 mg/kg of Cyclic Peptide 5, $P=2.3 \times 10^{-7}$.

In activity studies the synthetic cyclic tetradecapeptide Cyclic Peptide 5 (SEQ ID NO. 6), which was identified initially as having significant antifungal activity, was used as a model peptide. Briefly, 7-8 week old, immunocompetent, female BALB/c mice were challenged i.v. at T=0 with $3\times10^5$ CFU of *C. albicans* SC5314. Twenty-four hours post-infection, mice were treated i.p. with saline, fluconazole (Fluco), caspofungin (Caspo), or synthetic cyclic tetradecapeptide, once a day for 7 days. Inventors had previously determined that the model peptide Cyclic Peptide 5 was substantially more potent than the natural θ-defensin RTD-1 in this in vivo model, as 0.25 mg/kg of Cyclic Peptide 5 was more effective than 5 mg/kg of RTD-1. Both peptides were more effective than 5 mg/kg of fluconazole (see FIG. 9). Reducing the Cyclic Peptide 5 peptide dose to 0.1 mg/kg, however, provided no survival benefit (see FIG. 10).

Candidate synthetic cyclic tetradecapeptides were prescreened for tolerance by determining a lack of toxicity when administered at >5 mg/kg. Candidate synthetic cyclic tetradecapeptides were screened for efficacy in the candidiasis model describe above, with daily dosing of each peptide (0.1 and 0.5 mg/kg) for 7 days, beginning 24 hours post infection, comparing each candidate to the Cyclic Peptide 5 reference peptide and fluconazole.

Under these test protocols *C. albicans*-infected mice treated with saline presented with ruffled fur and significant

TABLE 2

| Analog name | | | | 1$^{st}$ β turn | | | | | | | 2$^{nd}$ β turn | | | | |
|---|---|---|---|---|---|---|---|---|---|---|---|---|---|---|---|
| | 3 | 4 | 5 | 6 | 7 | 8 | 9 | 10 | 11 | 12 | 13 | 14 | 1 | 2 | SEQ ID NO. |
| Cyclic Peptide 1 | C | S | C | R | R | R | F | C | L | C | R | R | G | V | SEQ ID NO 2 |
| Cyclic Peptide 2 | C | S | C | R | R | R | F | C | I | C | R | R | G | V | SEQ ID NO 3 |
| Cyclic Peptide 3 | C | I | C | R | R | R | V | C | I | C | R | R | G | V | SEQ ID NO 4 |
| Cyclic Peptide 4 | C | I | C | R | R | R | A | C | L | C | R | R | G | L | SEQ ID NO 5 |
| Cyclic Peptide 5 | C | I | C | R | R | R | F | C | L | C | R | R | G | V | SEQ ID NO 6 |
| Cyclic Peptide 6 | C | R | C | R | R | G | V | C | R | C | R | R | G | V | SEQ ID NO 7 |

Amino acid positions are designated according to the convention shown in FIG. 7A.

weight loss, and became moribund within 5-10 days, by which time there was >30% body weight loss. In contrast, long term surviving Cyclic Peptide 5-treated candidemic mice had a transient 15% mean reduction in bodyweight that plateaued by day 10, and 90% of this cohort regained initial body weights by day 3).

Utilizing the candidemia model, and survival as an efficacy metric, a number of synthetic cyclic tetradecapeptides were identified that were equivalent or superior to Cyclic Peptide 5. Among these were Cyclic Peptide 3, Cyclic Peptide 4, Cyclic Peptide 1, Cyclic Peptide 2, and Cyclic Peptide 6. Results from the in vivo disseminated candidiasis model for these are shown in FIGS. 10 to 15.

Figure 10:
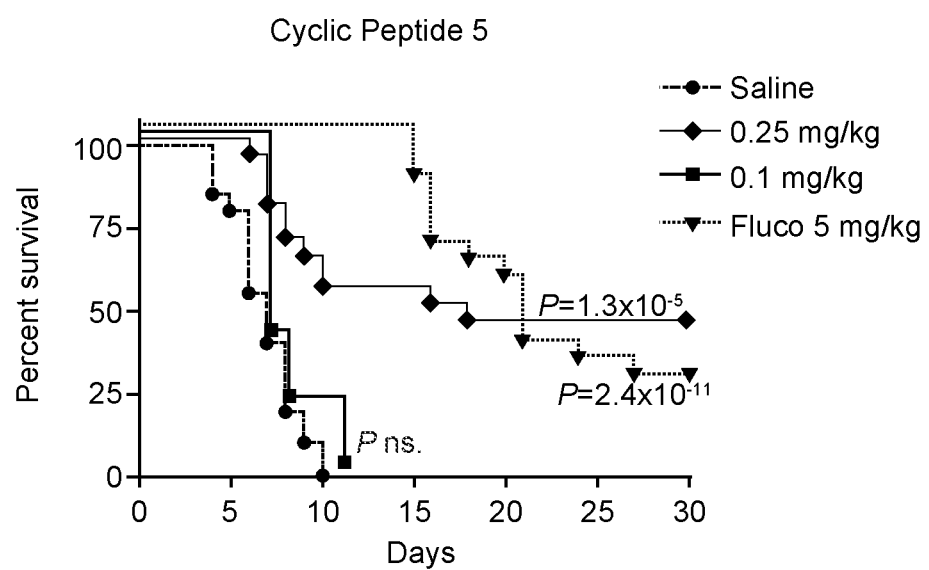
FIG. 10 shows typical results from a study of the effects of the synthetic cyclic tetradecapeptide Cyclic Peptide 5 at 0.25 mg/kg and 0.1 mg/kg and fluconazole (Fluco) at 5 mg/kg in an in vivo model of disseminated candidiasis. Mice were infected i.v. at T=0 with $3 \times 10^5$ blastospores of *C. albicans* SC5314. At T=24 h, mice were treated i.p. daily for 7 d w. Mice were observed for 30 days p.i, and survival enhancement analyzed by log-rank analysis.
Figure 11:
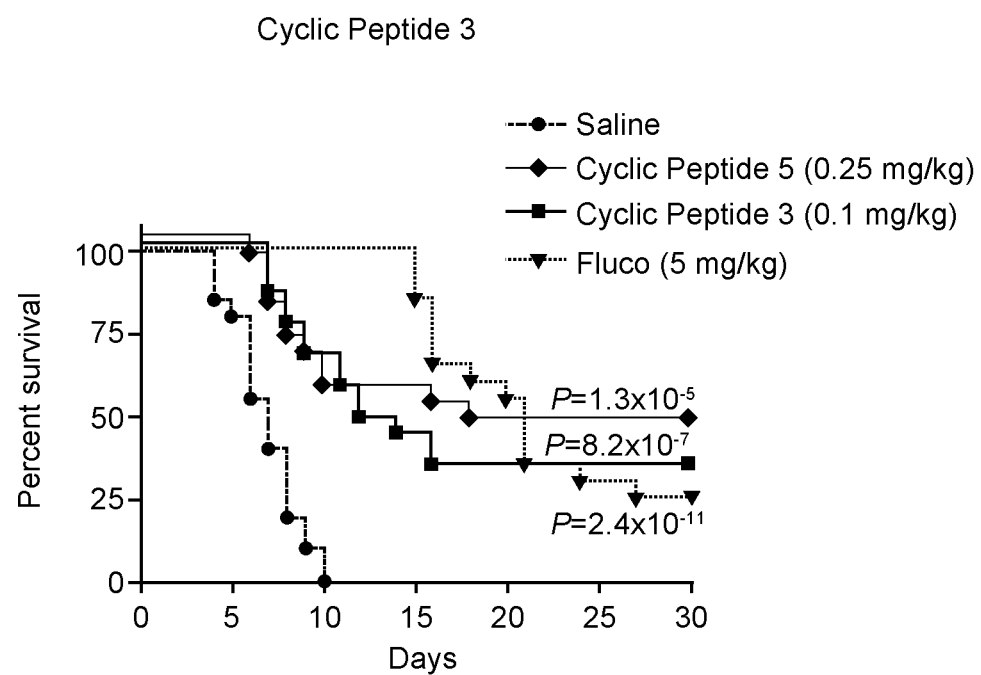
FIG. 11 shows typical results from a study of the effects of the synthetic cyclic tetradecapeptides Cyclic Peptide 5 at 0.25 mg/kg and Cyclic Peptide 3 at 0.1 mg/kg and fluconazole (Fluco) at 5 mg/kg in an in vivo model of disseminated candidiasis as in the studies shown in FIG. 10.
Figure 12:
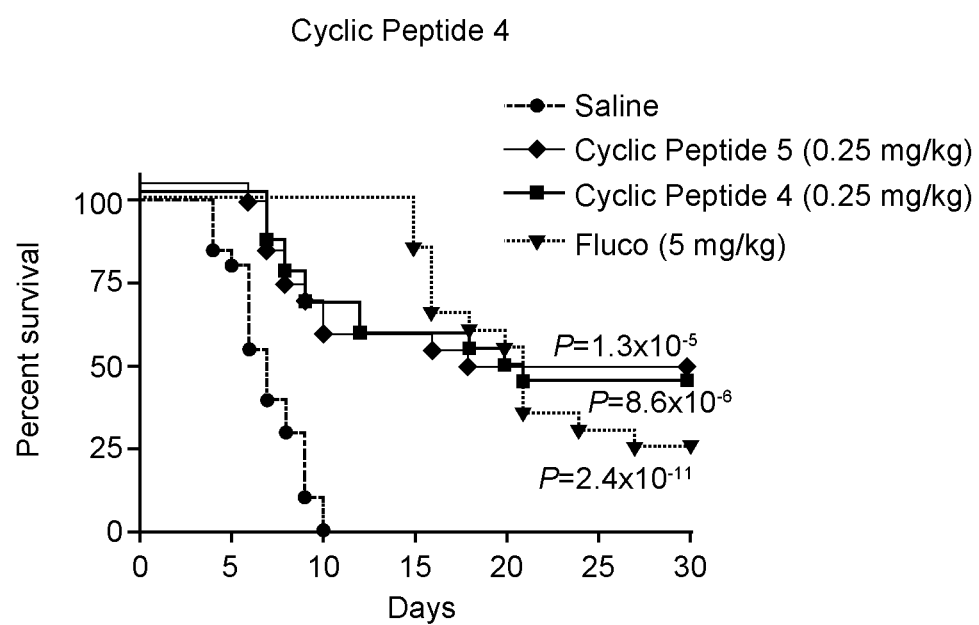
FIG. 12 shows typical results from a study of the effects of the synthetic cyclic tetradecapeptides Cyclic Peptide 5 at 0.25 mg/kg and Cyclic Peptide 4 at 0.1 mg/kg and fluconazole (Fluco) at 5 mg/kg in an in vivo model of disseminated candidiasis as in the studies shown in FIG. 10.
Figure 13:
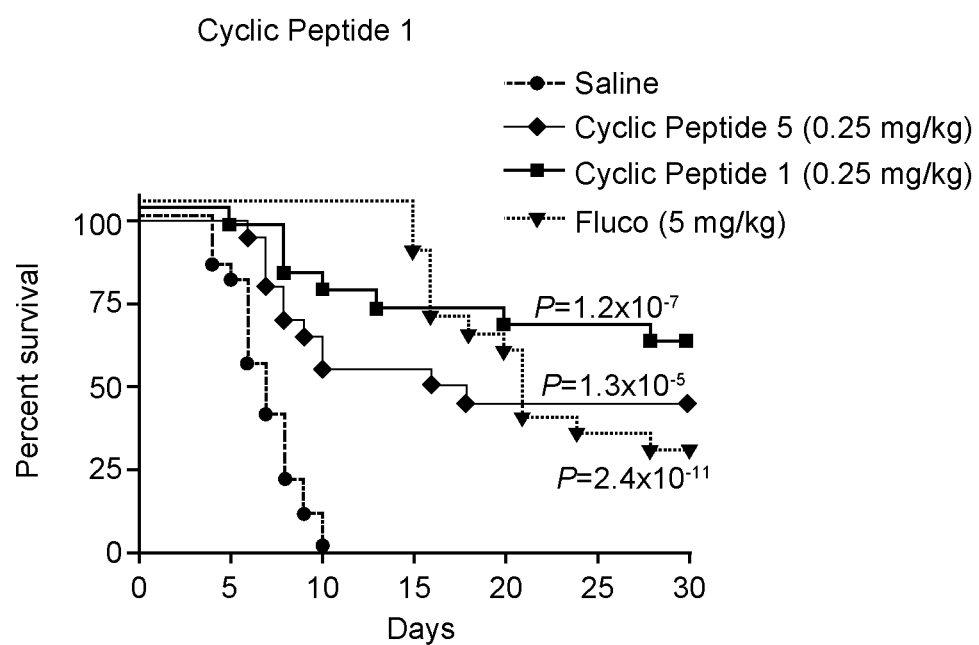
FIG. 13 shows typical results from a study of the effects of the synthetic cyclic tetradecapeptides Cyclic Peptide 5 at 0.25 mg/kg and Cyclic Peptide 1 at 0.1 mg/kg and fluconazole (Fluco) at 5 mg/kg in an in vivo model of disseminated candidiasis as in the studies shown in FIG. 10.
Figure 14:
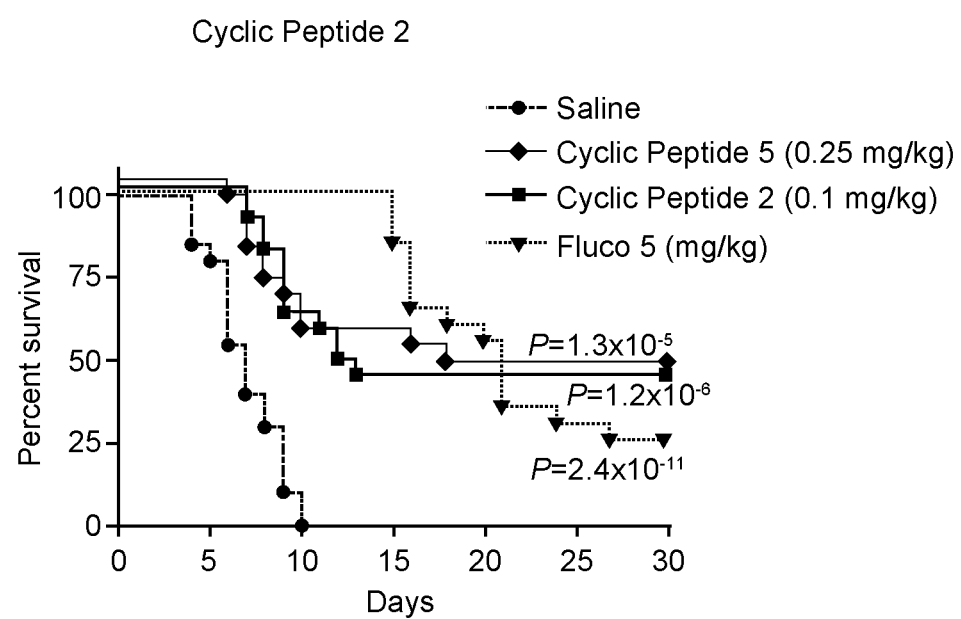
FIG. 14 shows typical results from a study of the effects of the synthetic cyclic tetradecapeptides Cyclic Peptide 5 at 0.25 mg/kg and Cyclic Peptide 2 at 0.1 mg/kg and fluconazole (Fluco) at 5 mg/kg in an in vivo model of disseminated candidiasis as in the studies shown in FIG. 10.

FIG. 10 shows typical results from testing using 0.25 mg/kg or 0.1 mg/kg of Cyclic Peptide 5. Cyclic Peptide 5 was found to be relatively ineffective, with results similar to treatment with saline. FIG. 11 shows typical comparative results between treatment with Cyclic Peptide 5 at 0.25 mg/kg and Cyclic Peptide 3 at 0.1 mg/kg. Cyclic Peptide 3 was found to be effective at this relatively low dose. FIG. 12 shows typical results from a comparative study of Cyclic Peptide 5 and Cyclic Peptide 4, with both peptides being used at 0.25 mg/kg. Cyclic Peptide 4 is effective at this dose. FIG. 13 shows typical comparative results between treatment with Cyclic Peptide 5 and Cyclic Peptide 1, with both peptides applied at 0.25 mg/kg. Cyclic Peptide 1 is effective at this dose. FIG. 14 shows typical results from a comparative study of Cyclic Peptide 5 at 0.25 mg/kg and Cyclic Peptide 1at 0.1 mg/kg. Cyclic Peptide 1 is effective at this relatively low dose.

Figure 15:
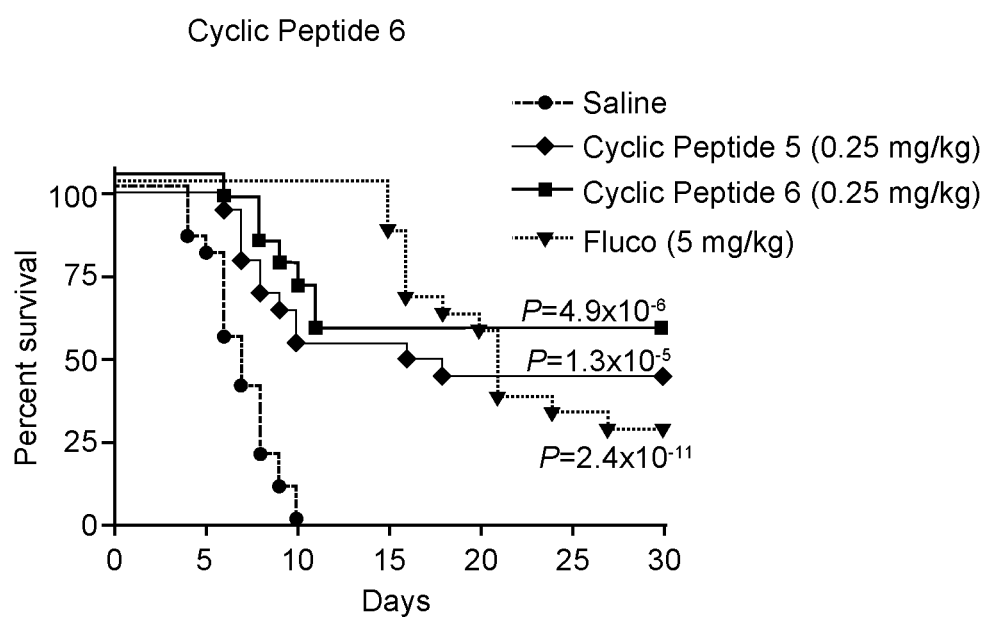
FIG. 15 shows typical results from a study of the effects of the synthetic cyclic tetradecapeptides Cyclic Peptide 5 at 0.25 mg/kg and Cyclic Peptide 6 at 0.1 mg/kg and fluconazole (Fluco) at 5 mg/kg in an in vivo model of disseminated candidiasis as in the studies shown in FIG. 10.

As noted above, Cyclic Peptide 6 differs from other peptides cited herein in lacking a triplet of consecutive (i.e., adjacent) arginine residues within a characteristic β turn portion of the peptide (defined by AA6, AA7, AA8, and AA9), and in having strongly basic arginine residues rather than hydrophobic amino acids within the characteristic C-X-C box of this family of circular peptides. FIG. 15 shows typical data from a comparative study between Circular Peptide 5 and Circular Peptide 6, with peptides used at 0.25 mg/kg. Cyclic Peptide 6 was found to provide survival that exceeded that of both a prior art antifungal drug (fluconazole) and Circular Peptide 5.

In each case, the specified synthetic cyclic tetradecapeptide enhanced survival, and the effect was highly significant ($P<1\times10^{-5}$, log-rank analysis). Cyclic Peptide 3, Cyclic Peptide 4, Cyclic Peptide 1, and Cyclic Peptide 6 were more effective than fluconazole in enhancing survival by end point analysis ($\chi^2$ analysis at day 30 p.i.). All of identified synthetic cyclic tetradecapeptides prevented significant weight loss in this in vivo model.

Renal fungal burden was determined in kidney homogenates from moribund saline-treated controls (day 5-10 p.i.) and from long term survivors (30 days p.i.). treated with synthetic cyclic tetradecapeptides or fluconazole. As shown in FIG. 16, synthetic cyclic tetradecapeptide (0.1 or 0.25 mg/kg) and 5 mg/kg fluconazole reduced fungal burden. Cyclic Peptide 5, Cyclic Peptide 3, Cyclic Peptide 4, and Cyclic Peptide 1 reduced fungal burden to a greater extent than fluconazole (asterisks in FIG. 16; analyzed by Fisher's LSD test: Cyclic Peptide 5 ($P=3\times10^{-3}$), Cyclic Peptide 3 ($P=7.4\times10^{-3}$), Cyclic Peptide 4 ($P=0.02$), and Cyclic Peptide 1 ($P=3.5\times10^{-5}$).

A number of sequence features were identified that confer superior activity to RTD-1 and Cyclic Peptide 5-derived analogs compared to these reference peptides. As noted above, Cyclic Peptide 3, Cyclic Peptide 4, Cyclic Peptide 1, and Cyclic Peptide 2 represent a group of synthetic cyclic tetradecapeptide θ-defensin analogs that show clear structural similarities. Inventors believe that θ-defensin analogs with significant antifungal and/or anti-inflammatory activity that are within this family can have at least:

- Two disulfide bonds, between Cys3 and Cys12 and between Cys5 and Cys10, respectively.
- Serine or a hydrophobic amino acid positioned between Cys3 and Cys5 and a hydrophobic amino acid positioned between Cys10 and Cys12 in the primary structure of the θ-defensin analog (i.e. at positions 4 and 11), where the hydrophobic amino acid is preferably leucine or isoleucine. In combination with the disulfide bonds noted above this defines a feature referred to as the "C-X-C box" within the circular primary structure of the peptide, where "C" is a cysteine and "X" is serine, leucine, or isoleucine.
- A total of five arginine residues that provide the peptide with a charge of +5 at physiological pH.
- A triplet of adjacent arginines at positions 6, 7, and 8, i.e. within the first β-turn.

In some embodiments active θ-defensin analogs can also include one or more of the following features:

- A glycine at position 1.
- Hydrophobic amino acids at position 2 and position 9, preferably valine or leucine.
- An arginine pair within the second β-turn (e.g. at positions 13 and 14).

Toxicity of candidate peptides suggests that active θ-defensin analogs should not include one or more of:

- An alanine at position 4.
- An alanine at position 11.

Accordingly, Inventors believe a synthetic cyclic tetradecapeptide θ-defensin analog that include a "C-X-C box" structure as described above, a triplet of adjacent arginine residues at positions 6, 7, and 8, a hydrophobic amino acid (e.g.valine or phenylalanine) at position 9, and having a net positive charge of +5 (about 36% of total amino acid content)) due to arginine content will be effective in reducing mortality and/or improving long term survival in disseminated fungal infections, and can be effective in treating other conditions characterized by dysregulation of an inflammatory or immune response.

Inventors believe that Cyclic Peptide 6 is representative of a different family of synthetic cyclic tetradecapeptide analogs of θ-defensins that have all or some of the above features, with the following exceptions:

- Presence of a plurality of two or more positively charged amino acids (e.g. arginine, lysine) within the C-X-C box
- Lack of a consecutive (i.e., adjacent) arginine triplet within the second β-turn defined by AA6, AA7, AA8, and AA9.

Synthetic cyclic tetradecapeptide analogs of θ-defensins as described herein can be applied using any suitable method. For example, such analogs can be provided by injection or infusion. The high degree of effectiveness observed for some θ-defensin analogs indicates that these can be provided to an individual in need of treatment in effective amounts by simple subcutaneous, intradermal, subdermal, and/or intramuscular injection.

Alternatively, the low molecular weight and high degree of stability conferred by circular structure and the presence of disulfide bonds can allow for oral administration of θ-defensin analogs of the inventive concept. Such oral administration can include administration of a solution or suspension of the θ-defensin analog in a liquid pharmaceutical carrier suitable for oral administration. In some embodiments a θ-defensin analog can be provided in a dry or lyophilized form that is reconstitute in a liquid media prior to oral administration. Such dry or lyophilized formulations can include a stabilizer. Suitable stabilizers include carbohydrates (e.g. mannitol, sucrose, trehalose) and/or proteins (e.g. albumin).

Alternatively, analogs of θ-defensin can be provided in a tablet, capsule, pill, or other suitable solid and compact form for oral administration. Such formulations can include coatings, shells, or similar components that provide for delayed release of the θ-defensin analog (for example, delaying release until reaching the small intestine). Such formulations can include the θ-defensin in liquid form within an enclosure or coating. Alternatively, such formulations can include a θ-defensin analog in a dry or lyophilized form. Suitable dry or lyophilized forms include powders, granules, and compressed solids. Such dry or lyophilized formulations can include a stabilizer. Suitable stabilizers include carbohydrates (e.g. mannitol, sucrose, trehalose) and/or proteins (e.g. albumin).

As noted above, θ-defensin analogs of the inventive concept can effectively treat disseminated fungal infections and associated sepsis and/or septic shock. In some embodiments such treatment is in response to an ongoing, acute condition. In other embodiments such treatment is prophylactic, for example used to prevent the development of disseminated fungal infection when the individual is suspected of having or has a high probability of developing this condition. Treatment can be provided by administration of a θ-defensin analog of the inventive concept on any suitable schedule. For example, a θ-defensin analog can be provided as a single dose, periodic doses, or as a continuous infusion. Periodic doses can be administered at any suitable intervals. Suitable intervals can be hourly, every 2 hours, every 4 hours, 4 times a day, 3 times a day, twice a day, once daily, every 2 days, every 3 days, twice a week, weekly, every 2 weeks, every 4 weeks, every 2 months, every 3 months, every 4 months, 3 times a year, twice a year, or annually.

In some embodiments the mode of administration for a θ-defensin analog can be modified during the course of treatment. For example, a θ-defensin analog of the inventive concept can initially be administered by intravenous injection or infusion (e.g. to rapidly provide effective concentrations in acute disseminated fungal infection), followed by intradermal injection, intramuscular injection, and/or oral administration in order to maintain an effective concentration over a remaining period of treatment.

For prophylactic use, a θ-defensin analog can be administered prior to the onset of observable symptoms. For treatment of an active disease or condition a θ-defensin analog can be administered for a period of suitable to effectively treat the disease or condition. Such a period can be over for a controlled period of time, or can be long term (e.g. for treatment of chronic conditions).

In some embodiments of the inventive concept a θ-defensin analog can be used in combination with other pharmaceutically active compounds. Suitable compounds include a θ-defensin, a different θ-defensin analog, an antifungal antibiotic, an antibacterial antibiotic, an antiviral, an anti-inflammatory drug (e.g. steroids, non-steroidal anti-inflammatory drugs), a vasopressor, and/or a biologic (e.g. antibodies or antibody fragments). Such additional pharmaceutical compounds can be provided on the same schedule as the θ-defensin analog, or on an independent schedule. In some embodiments a θ-defensin analog-containing formulation can be provided that incorporates one or more of such additional pharmaceutically active compounds. Inventors believe that such cotherapy can provide a synergistic effect in which the cumulative effect of administration of the θ-defensin analog in combination with the additional pharmaceutically active compound exceeds the sum of the individual effects observed with treatment using the θ-defensin analog and the additional pharmaceutically active compound in amounts corresponding to those used for cotherapy.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A cyclic peptide consisting of 14 amino acids and having the following structure:

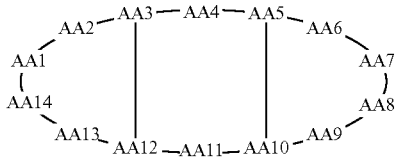

wherein AA1, AA2, AA13, and AA14 are amino acids, AA3 and AA12 are cysteines joined by a disulfide bond, AA5 and AA10 are cysteines joined by a disulfide bond, AA4 is serine or a hydrophobic amino acid, AA9 and AA11 are a hydrophobic amino acids, two of AA6, AA7, and AA8 are arginine, wherein a β turn segment of the cyclic peptide defined by AA6, AA7, AA8, and AA9 does not include more than two adjacent arginines, and wherein the cyclic peptide comprises five or more arginine residues that provide a positively charged content of at least about 36% at physiological pH, wherein the cyclic peptide has an antifungal activity.

2. The cyclic peptide of claim 1, wherein AA1 is glycine.

3. The cyclic peptide of claim 1, wherein AA2 is a hydrophobic amino acid.

4. The cyclic peptide of claim 1, wherein at least one of AA13 and AA14 is arginine.

5. The cyclic peptide of claim 1, wherein the cyclic peptide is an analog of a θ-defensin, and wherein the cyclic peptide provides improved survival when applied systemically in a murine disseminated candidiasis model relative to the θ-defensin.

6. The cyclic peptide of claim 1, wherein the cyclic peptide provides a biphasic response on application to a murine model of disseminated candidiasis, wherein the biphasic response comprises a first phase of mobilization of host effector cells having antifungal activity and a second phase of moderation of host inflammatory response.

7. The cyclic peptide of claim 1, wherein the cyclic peptide comprises a tumor necrosis factor alpha converting enzyme (TACE) inhibiting activity.

8. The cyclic peptide of claim 1, wherein the cyclic peptide suppresses at least one of expression, processing, and release of a proinflammatory cytokine.

9. The cyclic peptide of claim 1, wherein the cyclic peptide retains activity following exposure to environmental extremes of temperature, low pH, freezing and/or thawing, and dissolution in a biological matrix.

10. The cyclic peptide of claim 1, wherein the cyclic peptide is non-immunogenic at doses effective to treat disseminated fungal infection.

11. A cyclic peptide consisting of 14 amino acids and having the following structure:

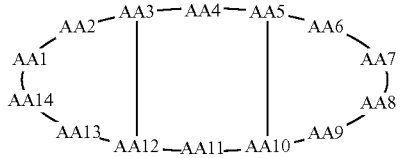

wherein AA1 is G, AA2 is V, AA3 is C, AA4 is R, AA5 is C, AA6 is R, AA7 is R, AA8 is G, AA9 is V, AA10 is C, AA11 is R, AA12 is C, AA13 is R, and AA14 is R, wherein AA3 and AA12 are joined by a cysteine bond, and AA5 and AA10 are joined by a cysteine bond.

* * * * *

SEQUENCE LISTING

```
<160> NUMBER OF SEQ ID NOS: 7

<210> SEQ ID NO 1
<211> LENGTH: 18
<212> TYPE: PRT
<213> ORGANISM: Macaca mulatta

<400> SEQUENCE: 1

Gly Phe Cys Arg Cys Leu Cys Arg Arg Gly Val Cys Arg Cys Ile Cys
1               5                   10                  15

Thr Arg

<210> SEQ ID NO 2
<211> LENGTH: 14
<212> TYPE: PRT
<213> ORGANISM: Artificial Sequence
<220> FEATURE:
```

```
<223> OTHER INFORMATION: Cyclic Peptide 1

<400> SEQUENCE: 2

Gly Val Cys Ser Cys Arg Arg Arg Phe Cys Leu Cys Arg Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Cyclic Peptide 2

<400> SEQUENCE: 3

Gly Val Cys Ser Cys Arg Arg Arg Phe Cys Ile Cys Arg Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Cyclic Peptide 3

<400> SEQUENCE: 4

Gly Val Cys Ile Cys Arg Arg Arg Val Cys Ile Cys Arg Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Cyclic Peptide 4

<400> SEQUENCE: 5

Gly Leu Cys Ile Cys Arg Arg Arg Ala Cys Leu Cys Arg Arg
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Cyclic Peptide 5

<400> SEQUENCE: 6

Gly Val Cys Ile Cys Arg Arg Arg Phe Cys Leu Cys Arg Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Cyclic Peptide 6

<400> SEQUENCE: 7

Gly Val Cys Arg Cys Arg Arg Gly Val Cys Arg Cys Arg Arg
1               5                   10
```